United States Patent [19]

Brisson et al.

[11] Patent Number: 5,331,952
[45] Date of Patent: Jul. 26, 1994

[54] WATER SYSTEM FOR LITHOTRIPTER

[75] Inventors: A. Glen Brisson, Kildeer; Exequiel D. Cruz, Arlington Heights; Dianne L. Vickers, Cary, all of Ill.

[73] Assignee: Bantum Tripter Joint Venture Partners, Columbus, Ohio

[21] Appl. No.: 856,352

[22] Filed: Mar. 23, 1992

[51] Int. Cl.$^5$ ............................................. A61B 17/22
[52] U.S. Cl. ........................................ 601/3; 367/147
[58] Field of Search ............... 128/24 EL, 660.03; 367/147, 166

[56] References Cited

U.S. PATENT DOCUMENTS 4,630,607 12/1986 Duinker et al. ............... 128/24 EL
4,697,588 10/1987 Reichenberger ............... 128/24 EL
5,046,483 9/1991 Ogura ............................ 128/24 EL Primary Examiner—Lee S. Cohen
Assistant Examiner—Brian L. Casler
Attorney, Agent, or Firm—Robert M. Wolters

[57] ABSTRACT

A water system is provided for an extracoporeal lithotripter. The reflector is aimed downwardly and has a spark gap at the first focus point thereof for generating a shock wave. A rubber diaphragm spans the lower end of the reflector. A water reservoir is provided along with pipes and a pump for circulating water from the reservoir to the reflector and back. A vacuum pump maintains pressure below ambient in the reservoir, the reflector and connecting pipes to control downward ballooning of the diaphragm.

10 Claims, 1 Drawing Sheet

WATER SYSTEM FOR LITHOTRIPTER

BACKGROUND OF THE INVENTION

Noninvasive lithotripters for the extracorporeal disintegration or destruction of kidney stones are now well known. Basically, an ellipsoidal reflector is utilized which is cut off at one end. An ellipsoid has two focus points, and a spark gap is provided at the first focus point. The reflector is filled with water. In initial efforts, both the reflector and the patient were emersed in a rather large water bath. More recent efforts have provided the cut off end of the ellipsoidal reflector with a rubber-like diaphragm. Typically, the reflector is placed in vertical position beneath a patient who lies on his back on a table with a cutout. The reflector is positioned in the cutout with the rubber diaphragm pressed against the patient's back in the area of the kidney. The position of the reflector is manipulated relative to the patient so that the kidney stone or other bodily concretion lies at the second focus point of the reflector.

Electrical energy is discharged across the spark gap in the form of a repeating series of sparks. Each spark flashes a certain amount of the water into steam, and may also produce some disassociation of the hydrogen and oxygen making up the water. In any event, a shock wave is generated. This shock wave passes through the water in the reflector, and is focused by the walls of the reflector on the second focus point. The shock wave energy passes through the water in the reflector and through the human tissues, which are 80% or more water, and focuses on the kidney stone. A repeated series of such shock waves reduces the kidney stone to fragments which pass out of the body with the urine.

Prior art extracoporeal or noninvasive lithotripters have been positioned with the reflector oriented substantially vertically upwardly. Gases produced by the sparks rise within the water in the lithotripter, and tend to accumulate beneath the diaphragm. This reduces the transmission efficiency of the shock wave from the reflector into the body tissues, and to the kidney stone or other concretion. Various structures and processes have been evolved to remove or to minimize the effect of such gases in the water.

The water pressure in the prior art systems has generally been substantially above ambient air pressure so as to cause the diaphragm to balloon upwardly for conformity with the patient's body. Such water systems in the prior art have generally been more or less permanently connected with water supplies, and this has limited mobility of the lithotripter apparatus. Such water systems have generally been rather complicated.

OBJECTS AND SUMMARY OF THE PRESENT INVENTION

It is an object of the present invention to provide a simple, reliable water system for an extracoporeal lithotripter.

It is a further object of the present invention to provide a lithotripter which need not be connected to a water system, and which therefore is much more readily movable than those of the prior art.

Still another object of the present invention is to provide an extracoporeal lithotripter which has a downwardly opening ellipsoidal reflector with a diaphragm at the bottom thereof, and with the water in the system at a pressure less than ambient pressure.

In carrying out the foregoing and other objects of the present invention we provide a water tank having a capacity of 20 liters, which is filled at the beginning of each day of operation, and emptied at the end of the day. The water is pumped about a rather simple circulatory system, generally from the tank or reservoir through a water pump to a reflector, and back to the reservoir or storage tank. At the end of the day the water is emptied into a drain or a relatively large storage tank.

The ellipsoidal reflector is positioned with its open end down, and with a rubber diaphragm closing the lower end. A vacuum is provided which maintains a negative pressure on the water relative to ambient, and thereby limits the force applied to the diaphragm by the water, thus protecting the diaphragm from too much pressure that might cause it to rupture while ballooning downwards, and also limiting the force applied to the patient.

THE DRAWINGS

The invention will best understood from a reading of the following specification when taken in connection with the accompanying drawings wherein.

DETAILED DESCRIPTION OF THE ILLUSTRATED EMBODIMENT

Figure 1:
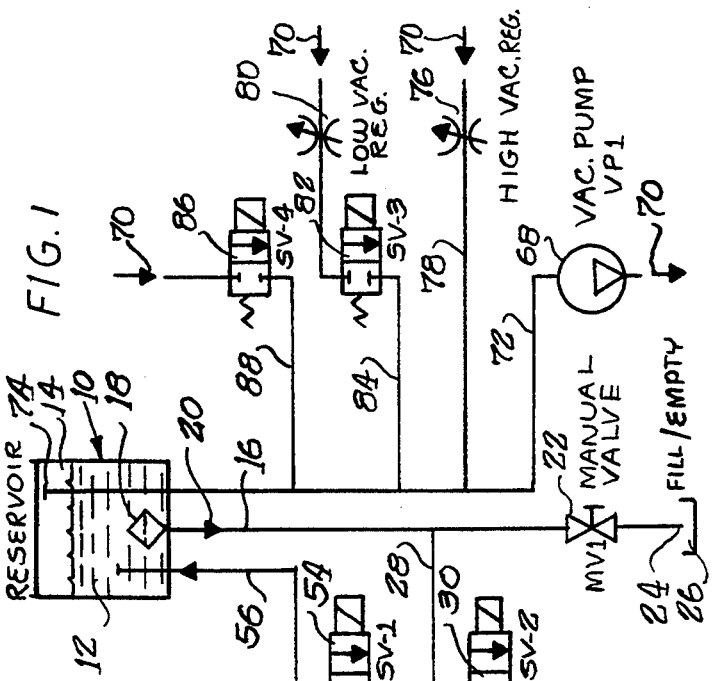
FIG. 1 is a schematic diagram illustrating the invention.

Referring first to FIG. 1, the lithotripter of the present invention embodies a reservoir or main water storage tank 10 made of stainless steel and having a capacity of 20 liters. The tank 10 is normally filled with 15 liters of water 12, leaving a 5 liter air space 14 above the water. The reservoir is sealed except for the pipes or water flow lines in and out of the tank.

A first water flow line or pipe 16 is connected to the reservoir in fluid communication with the water 12 therein. A filter 18 is provided at the top of the line and, except during filling and emptying of the reflector, water flow is outward from the reservoir through the line 16, as indicated by the arrowhead 20. Near the lower end of the pipe 16 there is a manual shutoff valve 22, and the lower end 24 of the pipe empties into a water reservoir or drain 26.

A branch line or pipe 28 extends from the pipe 16 (to the left in FIG. 1) to a solenoid controlled valve 30. The condition of open or closed of this valve as well as that of other valves will be set forth in detail hereinafter. From the solenoid valve 30 a pipe 32 leads to a water pump 34. A pipe 36 leads from the water pump to the ellipsoidal reflector 38 of the lithotripter. The bottom end of the lithotripter is open at 40, and a rubber diaphragm 42 underlies the open end of the reflector. A pair of electrodes 44 extend through the wall of the reflector at 38 and form a spark gap 46 precisely at the first focus point of the reflector. The second focus point of the reflector is indicated by a cross at 48 beneath the bulged out or ballooned diaphragm 42. One shock wave path is shown in dotted lines to each side, but it will understood that there are a myriad of similar paths leading from the spark gap 46 to the walls of the reflector and on to the second focus point 48. The reflector is made of brass, and the electrodes obviously are insulated from the wall of the reflector. An electric shock wave generator 50 is connected to the electrodes 44 for causing a succession of sparks to pass between the electrodes over the gap 46.

The pipe 36 opens into the reflector relatively near the open lower end 40, an outlet pipe 52 is connected to the reflector at the apex 54 thereof. The pipe 52 passes to a solenoid controlled valve 54 which is connected to a pipe 56 leading into the reservoir 10. A branch line or pipe 58 extends laterally from the pipe 52 to a solenoid controlled valve 60. An outlet pipe 62 from this solenoid valve is connected to a hydrophobic filter 64. A pipe 66 extends from the hydrophobic filter, and the connection at the other end of the pipe 66 will be set forth hereinafter.

A vacuum pump 68 includes an electric motor for driving the pump to produce a vacuum. The vacuum pump has a vent to ambient air condition indicated by the arrow 70, and a similar arrow 70 pointing into the top of the line or pipe 66 indicates that the pipe 66 vents to ambient air at this position. A low pressure pipe 72 also leads from the vacuum pump and extends to a termination 74 within the reservoir, and specifically in the air space 14 above the water 12. Another arrow 70 indicating further venting to ambient air leads to a high vacuum regulator device 76, the opposite side of the high vacuum regulator device being connected by a pipe 78 to the pipe 72. Similarly, another arrow 70 indicates ambient air connected to a low vacuum regulator device 80 which is connected to a solenoid operated valve 82, and through this valve to a pipe 84 leading to the pipe 72.

Ambient air also is connected indicated by the arrow 70 to a solenoid controlled valve 86 leading to a line or pipe 88 which is connected to the pipe 72.

Figure 2:
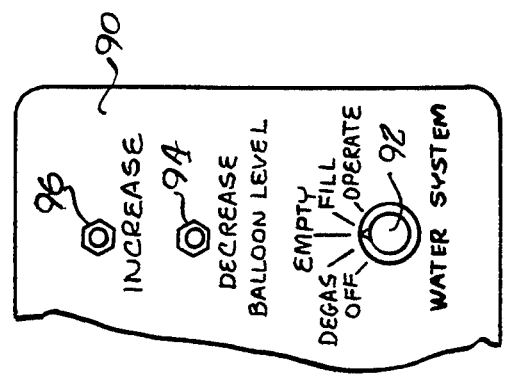
FIG. 2 is a fragmentary diagram showing a portion of the control panel relative to the water system.

Control for the water system illustrated in FIG. 1 is shown in FIG. 2. A panel 90 carries a shaft (not shown) having a manually operable knob 92 with appropriate switch connections on the far side of the panel (not shown) for controlling five modes of operation of the water system. These modes, as labeled on the panel, comprise: OFF, DEGAS, EMPTY, FILL, and OPERATE. In addition, pushbutton switches 94 and 96 are mounted on the panel 90 respectively to decrease or to increase the balloon level, i.e. the degree to which the diaphragm balloons out from the reflector. These switches are of the type that are closed only when the manually held in.

Figure 3:
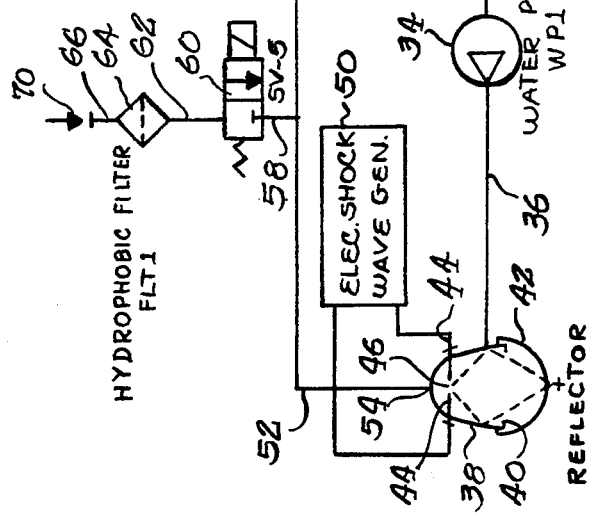
FIG. 3 is a chart showing operation of the various portions of the water system at different portions of a cycle thereof.

A table or chart in FIG. 3 indicates the condition of various of the solenoid controlled valves, and also the water pump and the vacuum pump or different ones of the operational modes. Besides being identified by numeral in FIG. 1, the solenoid controlled valves are labeled as SV-1 thru SV-5. Specifically, solenoid valve 54 is SV-1, solenoid controlled valve 30 is SV-2, solenoid controlled valve 82 is SV-3, solenoid controlled valve 86 is SV-4, and solenoid controlled valve 60 is SV-5. The first column of the table is identified as function, and the 5 operational modes are listed below.

The next five columns are labeled as SV-1 thru SV-5, the next column being labeled WATER PUMP, and the last column being labeled VACUUM PUMP. In the table the letter C is used to indicate when a solenoid controlled valve is closed, while the letter O is used to indicate when a valve is open. The water pump and the vacuum are respectively indicated as OFF or ON.

Operation of the water system will now be described:

Degas

The Degas mode is used to remove any gas that may be present in the water. It is to be assumed that the reservoir 10 is full at this stage. The water in the reservoir is subjected to a vacuum of 20 inches of mercury to remove any gas. In the chart of FIG. 3, it will be seen that solenoid valves SV-1 thru SV-4 are closed. Valves 1 and 2 isolate the tank or reservoir from the reflector 38. Valves 3 and 4 allow the vacuum pump 68, which is on, to produce the vacuum set on the high vacuum regulator 76. Solenoid valve 5 is open to allow air venting of the reflector assembly.

Fill

The fill mode is used to take water from the main tank and to fill the reflector prior to patient treatment. To allow water to circulate through the reflector, solenoid valves 1 and 2 are open, as will be seen opposite the "FILL" function. The water pump is turned on, as also will be seen in FIG. 3. This will cause water to be drawn from the main tank or reservoir through solenoid controlled valve 30 (SV-2), the water pump 34, and the reflector at 38 inlet to fill the reflector. Then water is pushed from the reflector outlet through the pipe 52 and solenoid controlled valve 54 (SV-1), which is open. Solenoid valve 86 (SV-4) is also open, thus allowing the reservoir 10 to remain at atmospheric pressure. The vacuum pump at this time is off because no vacuum on the main tank is required. Solenoid valve 60 (SV-5) is closed because the reflector is not vented at this time.

Operate

The Operate mode is used during ultrasonic imaging and patient treatment. In the operate mode a continuous flow of 3.0 liters per minute of water is passed through the reflector. This is required to remove gas bubbles caused by the sparks or electrical discharges across the gap 46 between the electrodes 44.

As may be seen on the diagram of FIG. 3 solenoid valves SV-1 and SV-2 are open, and the water pump is on to cause the water to circulate from the tank through the pump, through the reflector assembly, and back to the tank. Solenoid controlled valve 82 (SV-3) is open, and solenoid controlled valve 86 (SV-4) is closed, and the vacuum pump is turned on. This causes the low vacuum regulator 80 to set the vacuum in the main tank at about 3.5 inches of mercury. This low vacuum is required to balance some of the weight of the water in the reflector, and thus to keep the pressure of the membrane against the patient at the optimum level of best energy transfer. Solenoid controlled valve 60 (SV-5) is closed to prevent any air from being pulled into the system from the outside atmosphere.

Empty

The Empty mode is used to move the water from the reflector to allow for the changing of electrodes, or at the end of the operational day. As will be seen from the chart or table of FIG. 3, in the empty mode the solenoid controlled valve 54 (SV-1) is closed and the solenoid controlled valve 30 (SV-2) is open. Solenoid controlled valves 82 (SV-3) and 86 (SV-4) are closed and the vacuum pump is turned on. This allows the high vacuum level to be developed within the main tank. Solenoid controlled valve 60 (SV-5) is open to vent the reflector assembly to the atmosphere, and the water pump is turned off.

This combination allows water to be pulled from the lower port of the reflector assembly so normally the water in that can come up back through the water pump 34 and into the main tank. The space created by the water being removed from the reflector assembly is filled by air vented through solenoid valve 60 (SV-5). When the reflector is empty the system should be switched either to the DEGAS or OFF mode.

Off

The OFF mode is used when it is desired to keep the machine turned on but not in use. With reference to the table of FIG. 3, in the off mode solenoid valves 54b (SV-1), 30 (SV-2) and 82 (SV-3) are closed. This isolates the reflector from the main tank or reservoir 10. Solenoid controlled valves 86 (SV-4) and 60 (SV-5) are open. This vents the reflector and the main tank to atmospheric pressure. The water and vacuum pumps are turned off because they are not needed at this time.

Note that the hydrophobic filter 64 is located in series with solenoid valve 60. This filter is used as a safety device to keep any water from being forced out of the system when solenoid controlled valve 60 is open.

The water used for the system is distilled mixed with normal saline at the ratio of 1,000 ml of water to 17 ml of normal saline. Tap water can also be used if it has a conductivity of 150 to 400 umhos as measured on a standard conductivity meter.

When water is to be added to the system for operation of the lithotripter, the water system is switched to the DEGAS mode, and the pipe or tubing connected to the manual valve 22 is placed into the water supply. This can be any container filled with the required amount of water. The manual valve 22 is opened, and water is pulled into the main tank by the vacuum in the tank. After the required amount of water is transferred into the tank the manual valve is closed and the water system is left in the degas mode to remove any gas from the water.

At the end of the patient treatment day the water is removed from the main tank. To effect this, the water system is placed in the off mode and the manual valve 22 is open. The water will drain from the main tank through the pipe or tubing 16, through the manual valve 22, and out the termination 24 into the container, or alternately into a drain. When all the water has been drained from the tank, the manual valve 22 is closed and the water in the tank can be emptied into a drain. Reference previously has been made to the pushbutton switches 94 and 96 shown in FIG. 2. The switches are used in the OPERATE mode to make small adjustments in the amount of water in the reflector assembly, and therefore the degree of inflation of the balloon formed by the outwardly bulging diaphragm 42. In the operate mode pressing the INCREASE switch 96 closes solenoid valve 54 (SV-1) for the period of time that the button is held depressed. This allows water to flow into the reflector, but blocks the return of the water to the main tank, whereby the rubber membrane is inflated to a greater degree. When the DECREASE switch 94 is pushed solenoid valve 30 (SV-2) is closed. This allows water within the reflector to be pulled back into the main tank by the low vacuum in the main tank, but it stops any water from entering the reflector. This causes the membrane to deflate. The switches 94 and 96 are used only for fine adjustments during the OPERATE mode as when the reflector is moved closer to or further away from the patient during the ultrasound scanning and locating process.

Full operation of the present lithotripter as set forth in a patent application soon to be copending with this one (B&L Case 1), but a full understanding of that is not necessary to understand operation of the present invention. Aiming of the reflector can be done as set forth in the copending case, or by conventional means. The important thing is that the patient lies on a table on his abdomen, and the reflector is pushed against his back so as to locate the second focus point 48 on the kidney stone or other concretion to be disintegrated. The water system is operated as just disclosed, and the electric shock generator is operated to produce a series of sparks across the gap 46. The shock waves so produced are focused on the kidney stone and in due course reduces it to fragments that easily pass out with the urine.

The specific example of the present invention as herein shown and described is for illustrative purposes only. Various changes in structure will no doubt occur to those skilled in the art, and will be understood as forming a part of the present invention insofar as they fall within the spirit and scope of the appended claims.

The Invention is Claimed as Follows:

1. A water system for a lithotripter comprising a reflector aimed downwardly and having an open lower end and said reflector having a focus point and means in said reflector for generating a shock wave at said focus point, a rubber diaphragm spanning said reflector open lower end, a water reservoir, means for transporting water from said reservoir to said reflector and back to said reservoir and means for maintaining pressure below ambient air pressure in said reflector, said reservoir and said transporting means to control downward ballooning of said diaphragm.

2. A water system as set forth in claim 1 wherein said reservoir is sealed and has air at the top thereof, and further including a vacuum pump connected to the air at the top of the reservoir to maintain said pressure below ambient.

3. A water system as set forth in claim 2 and further including water conveying means connected to said reservoir and to a source of water at ambient pressure to convey water from said source through said conveying means into said reservoir by a pressure differential.

4. A water system as set forth in claim 3 and further including valve means in said water transporting means for isolating said reflector from said reservoir when water is being conveyed into said reservoir.

5. A water system as set forth in claim 2 wherein said water transporting means includes a branch from said reflector back to said reservoir, and further including air vent means, and a valve connecting said branch to said air vent means to vent air from water in said branch.

6. A water system as set forth in claim 5 wherein said air vent means includes a hydrophobic filter.

7. A water system as set forth in claim 2 and further including an air line between said vacuum pump and air in said reservoir, and air pressure regulating means connected to said air line for regulating air pressure at the top of said reservoir.

8. A water system as set forth in claim 7 wherein said pressure regulating means comprises at least two pressure regulators for regulating different ranges of air pressure.

9. A water system as set forth in claim 2 and further including means for stopping said vacuum pump, and means for venting said reservoir to ambient air pressure during initial transportation of water from said reservoir to said reflector.

10. A water system comprising a sealed reservoir, water conveying means connected to said reservoir and having means for connection to a source of water at ambient air pressure, a vacuum pump connected to air at ambient pressure, an airline connecting said vacuum pump to said water reservoir adjacent the top thereof, reduced air pressure in the top of said reservoir thereby conveying water through said water conveying means from said source to said reservoir by differential air pressure, and means for venting said reservoir adjacent the top thereof to ambient air pressure for permitting removal of water from said reservoir through said water conveying means.

* * * * *